United States Patent [19]

McRae

[11] Patent Number: 5,069,223
[45] Date of Patent: Dec. 3, 1991

[54] METHOD OF EVALUATING TISSUE CHANGES RESULTING FROM THERAPEUTIC HYPERTHERMIA

[75] Inventor: Donald A. McRae, Chevy Chase, Md.

[73] Assignee: Georgetown University, Washington, D.C.

[21] Appl. No.: 480,050

[22] Filed: Feb. 14, 1990

[51] Int. Cl.$^5$ .............................................. A61B 5/05
[52] U.S. Cl. ................................................... 128/734
[58] Field of Search ............................. 128/734, 804

[56] References Cited

U.S. PATENT DOCUMENTS

| | | | |
|---|---|---|---|
| 4,252,130 | 2/1981 | Le Pivert | 128/734 |
| 4,291,708 | 9/1981 | Frei et al. | 128/734 |
| 4,688,580 | 8/1987 | Ko et al. | 128/734 |
| 4,821,725 | 4/1989 | Azam et al. | 128/804 |

FOREIGN PATENT DOCUMENTS 1364297  1/1988  U.S.S.R. .............. 128/734

OTHER PUBLICATIONS

1) "Measurement of Intratissue Bioelectrical Low Frequency Impedance: A New Method to Predict Per-Operatively the Destructive Effect of Cryosurgery", Le Pivert et al., *Cryobiology*, 14, 245–250 (1977).
2) "Tissue Impedance and Temperature Measurements in Relation to Necrosis in Experimental Cryosurgery", Gage et al., *Cryobiology*, 22, 282–288 (1985).

Primary Examiner—Lee S. Cohen
Assistant Examiner—Krista M. Pfaffle
Attorney, Agent, or Firm—Oblon, Spivak, McClelland, Maier & Neustadt

[57] ABSTRACT

A method of evaluating tissue changes in a mammal occurring as a result of applying a therapeutic hyperthermia treatment to a volume of tissue of the mammal, which entails:
a) placing electrodes on, near or into the volume of tissue to be monitored;
b) applying therapeutic hyperthermia to the volume of tissue desired to be heated;
c) measuring the electrical impedance of the volume of tissue to be monintored at least twice by means of the electrodes and by impedance measurement means in order to measure frequency dependent changes in the measured electrical impedance;
d) employing the frequency dependent changes in the measured electrical impedance to evaluate physiological and histological changes in the tissue cells, thereby measuring the nature and extent of the tissue changes; and
e) employing the measurements obtained from the tissue changes as a predictive assay of the progress of the hyperthermia treatment, thereby employing the same as an aid in adjusting the administration of the treatment, or determining a prognosis for each treatment, or ascertaining the desired stopping point for each treatment, or determining the need for further treatment, or any combination of the above.

10 Claims, 9 Drawing Sheets

METHOD OF EVALUATING TISSUE CHANGES RESULTING FROM THERAPEUTIC HYPERTHERMIA

BACKGROUND OF THE INVENTION

1. Field of the Invention

The present invention relates to a method of evaluating tissue changes resulting from therapeutic hyperthermia by measuring the changes in the electrical impedance of the tissue.

2. Description of the Background

The electrical properties of cells and tissues have long been of interest to scientists. This has been particularly true since techniques for resistance and impedance measurements have become available. An early experiment by Hoeber demonstrated that very high frequencies and low frequencies yield different conductivity values for erythrocytes. This determination represented the first time that the existence of biological membranes was deduced from an electrical experiment.

The bulk electrical properties of tissues and cells are important as they determine the pathways of current flow through the body. Such properties are, therefore, important in the measurement of physiological parameters using impedance techniques, studies of biological effects of electromagnetic fields, electrocardiography, muscle contraction and nerve transmission.

Mammalian tissue may be viewed as a conglomeration of cells surrounded by membranes comprised of lipid and protein. These membranes resist the flow of ions and electric current thereacross and thus behave as electrical capacitive elements. Thus, intact healthy tissue resists electrical current. If the tissue is damaged such that the cells no longer maintain their membrane characteristics, the damaged membrane or damaged cells exhibit a reduced resistance or greater conductivity.

Recently, renewed interest in the use of hyperthermia for the treatment of cancer has considerably increased biological research on the molecular mechanisms and cellular alterations involved in heat-induced cell death. This relatively new cancer treatment technique, in which a volume of tissue in the body is heated to well above normal body temperature to promote the death of tumor cells, is presently being subjected to extensive laboratory investigation and clinical trials. Although hyperthermic techniques for the treatment of cancer have exhibited promise, the mechanism of heat-induced cellular alterations responsible for cell death remains unclear. Considerable evidence implies, however, that the cell membranes are one of the primary targets of hyperthermia damage.

Furthermore, in applying therapeutic hyperthermia in the clinic, an improper thermal dose can lead to severe clinical complications or to a lower probability of tumor control. At present, correlation of temperature measurements with laboratory findings or gross clinical data is the only method of assessing the thermal dose. Unfortunately, this means of correlation is frequently inadequate for an accurate prognosis.

Thus, a need continues to exist for a means by which the thermal dose to tissues in hyperthermic treatments can be accurately measured. Additionally, an accurate method is also needed for monitoring the progress of hyperthermic treatments.

SUMMARY OF THE INVENTION

Accordingly, it is an object of the present invention to provide a method for monitoring the progress of hyperthermic treatments.

It is also an object of the present invention to provide a method for defining and accurately measuring the thermal dose delivered to tissues in hyperthermic treatments.

It is further an object of the present invention to provide a method for evaluating tissue damage resulting from therapeutic hyperthermia.

It is, moreover, an object of the present invention to provide a method for evaluating tissue changes post-treatment.

Additionally, it is also an object of the present invention to provide a method for providing information on the physiological changes occurring during and after therapeutic hyperthermia.

Accordingly, these objects and others which will become more apparent in view of the following disclosure, are provided by a method of evaluating tissue changes in a mammal occurring during therapeutic hyperthermia, which entails:

a) applying therapeutic hyperthermia to a mammal and monitoring the changes in tissue electrical impedance before, during or after the application of said therapeutic hyperthermia or any combination thereof, and b) determining the extent of tissue change in the mammal from the progressive changes in tissue electrical impedance.

DETAILED DESCRIPTION OF THE PREFERRED EMBODIMENTS

Figure 1:
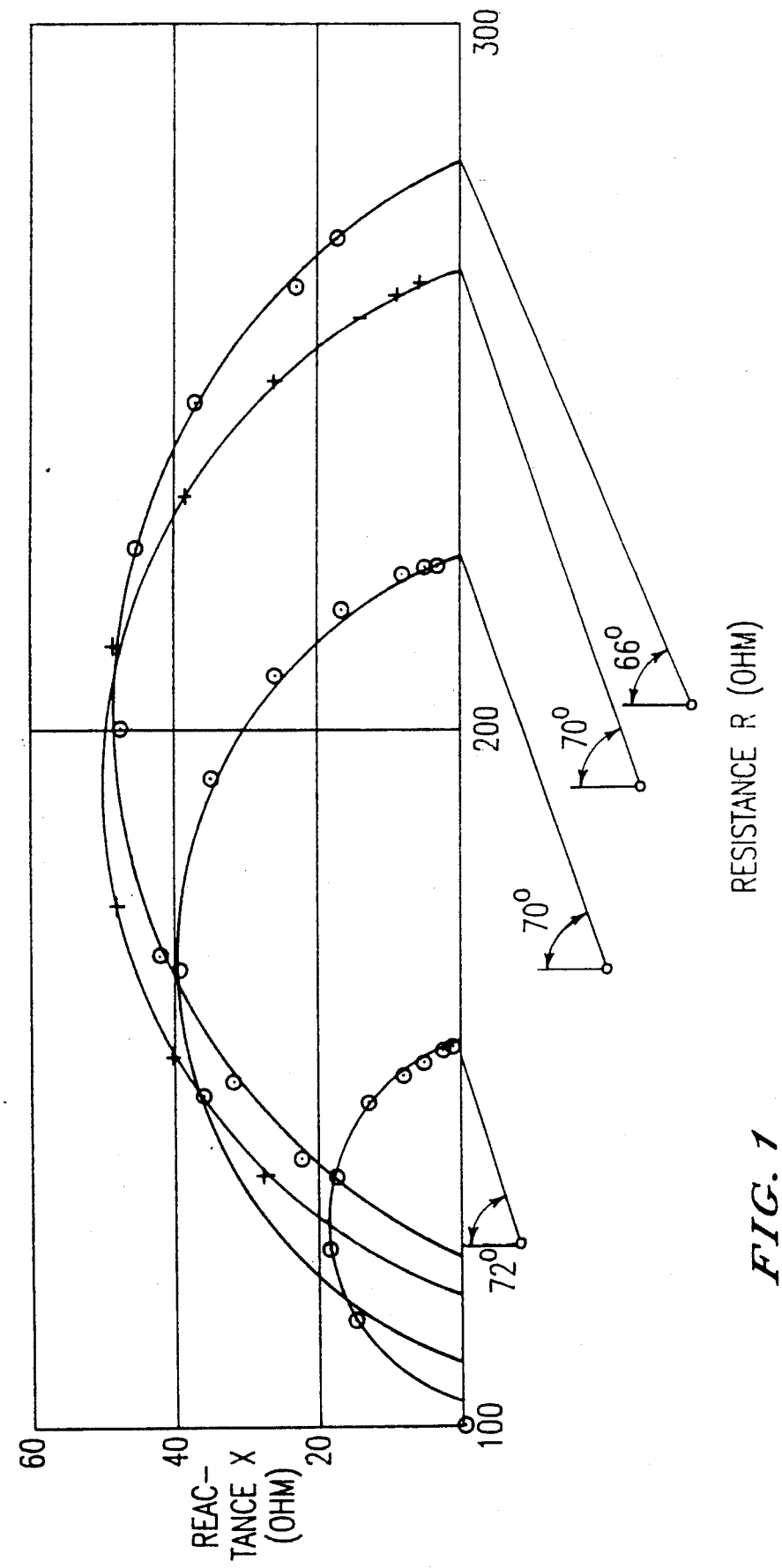
FIG. 1 illustrates a plot of the electrical reactance versus resistance of excised skeletal muscle from a frog and represents the $\beta$- dispersion of the tissue.

In accordance with the present invention, a method is provided for evaluating tissue changes resulting from therapeutic hyperthermia by measuring the changes in the electrical impedance of the tissue. The impedance changes can be correlated with tissue changes which are indicative of changes in the cell membrane characteristics. These impedance changes can be used to monitor subtle tissue changes which occur during therapeutic application of heat to tissues.

In accordance with the present invention, the electrical impedance of a volume of tissue is measured at one or more frequencies between about 1 Hz and 100 MHz using electrodes, either within, on the surface of, or near that volume of tissue. Although the electrodes used may be stationary, they may also be moved to sample the electrical impedances at or between various points. Although a frequency from between about 1 Hz to about 100 MHz may be used, in accordance with the present invention, it is preferred to use a frequency between about 1 KHz and 100 MHz. It is even more preferred to use a frequency range of about 10 KHz to 30 MHz. The changes in the electrical impedance at the different frequencies may then be used to monitor changes occurring within the tissue as a result of therapeutic hyperthermia. From the information obtained, conclusions may then be drawn about the damage occurring to the tissue, the physiological changes occurring, and/or the clinical effect of the therapy.

The above recited frequency ranges are advantageous in accordance with the present invention inasmuch as cell membranes are generally considered to be one of the primary targets of hyperthermia damage to tissues. Hence, when a tissue is subjected to therapeutic hyperthermia, the ultimate cell response, i.e., damage, will be reflected to some extent in changes in the membrane characteristics. Since the low frequency electrical impedance of tissues is to a large extent a function of the characteristics of the cell membranes, the in vivo measured impedance will vary with the hyperthermic effect on the membranes, and will provide data from which the clinical effects of the heating can be determined and monitored.

The present invention may be used to measure impedance changes both in vivo and in vitro. However, it is specifically recognized that the most useful applications of the present invention will occur with in vivo clinical applications. Moreover, although the present invention may be applied to practically any tissue in the body of interest, it has been found that the present invention is particularly useful when applied to soft tissues in the mammalian body. For example, excellent results may be obtained when applying the present invention to kidney tissue, liver tissue, muscle tissue and solid tumors of almost all varieties. The wide range of solid tumors which have been treated by hyperthermia is well known to those skilled in the art.

Generally, in measuring the electrical impedance of tissues in vivo, an alternating electric field is created between two or more electrodes, or two parts of a single electrode, and the magnitude and phase of the resulting electrical current is measured by means of a phase-sensitive measurement instrument or circuit. Alternatively, an electrical current may be applied and the amplitude and phase of the voltage are then measured. In making these measurements, it is recognized that either the so-called "two electrode technique" or "four electrode technique" can be employed. From this, two components of electrical impedance can be determined and used to analyze the condition of the tissue volumes measured. Also, even the raw measured data alone may be so used.

Furthermore, two general categories of electrodes may be used in the present invention. That is, either invasive or non-invasive electrodes may be used. The invasive electrodes are generally conductive devices of a particular known size and shape which are introduced into the tissue itself. The non-invasive electrodes are electrically conducting devices which are placed on or near the exterior of the volume of tissue under investigation. For example, electrodes similar to those used for EKG monitoring may be used. Also, a combination of any of these categories of electrodes may be used.

The electrical impedance is then measured between pairs or groups of electrodes, or between electrically separate portions of a single electrode, such as, for example, before, during and/or after the application of therapeutic hyperthermia. The changes in electrical impedance of a volume of tissue due to tissue or cell damage or change will be responsible for the main portion of the information received, but changes due to the temperature coefficients of the tissue constituents and blood volume or flow changes will also be manifested. However, it is estimated that changes due to the blood volume or flow changes are likely to only be up to about 10% of the total impedance change. That is, the overwhelming portion of impedance change will be due to tissue or cell damage or change. Also, changes due to temperature coefficient (usually less than or equal to about 2% per degree centigrade) can be estimated at measurement frequencies above the range where the tissue changes due to damage manifest themselves or can be estimated or determined from temperature measurements.

From the above information, the amount, extent and type of tissue or cell damage or change may be ascertained as well as the changes in blood volume. This information is then used for clinical control or evaluation of the therapeutic hyperthermia.

The electrical impedance of a material is a complex variable consisting of two mathematical components. These two components can be derived from the total measured impedance in a number of ways, such as capacitance and conductance, resistance and reactance, impedance magnitude and phase, for example. Moreover, the electrical impedance of tissues has certain characteristics which distinguish it from other materials. In the frequency ranges used, certain dispersions and their impedance properties are observed such as $\alpha$-and $\beta$-dispersions. These dispersions have been recognized in the art. See for example, "Electrical Properties of Cells: Principles, Some Recent Results, and Some Unresolved Problems" by H. P. Schwan, from *The Biophysical Approach to Excitable Systems* (Plenum Publishing Corporation, 1981). These dispersions characterize the tissue and its condition at the time measured. These dispersions can be characterized by the components of the electrical impedance as a function of frequency. Thus, the change in these components in the electrical impedance as a function of frequency, with time, are used to characterize the change in the tissue being measured. For example, the electrical conductivity and/or permittivity, or the resistivity and/or reactivity, or tangent delta, may be used as measures of the type and amount of tissue changes.

FIG. 1 is a graph with accompanying text from "Electrical Properties of Tissue and Cell Suspensions", in *Advances in Biological and Medical Physics Vol. 5*, pgs. 147–209, 1957 by H. P. Schwan. The plot is of the electrical reactance versus resistance of excised skeletal muscle from a frog and represents the "$\beta$-" dispersion of the tissue. The tissue has been excised and left at room temperature to deteriorate. The times indicate the time since excision. It is noted that over a time of several days, the semi-circular curves decrease in size toward the origin of the graph. This is interpreted to indicate the breakdown in cellular structure after the metabolic activity has ceased.

Figure 3:
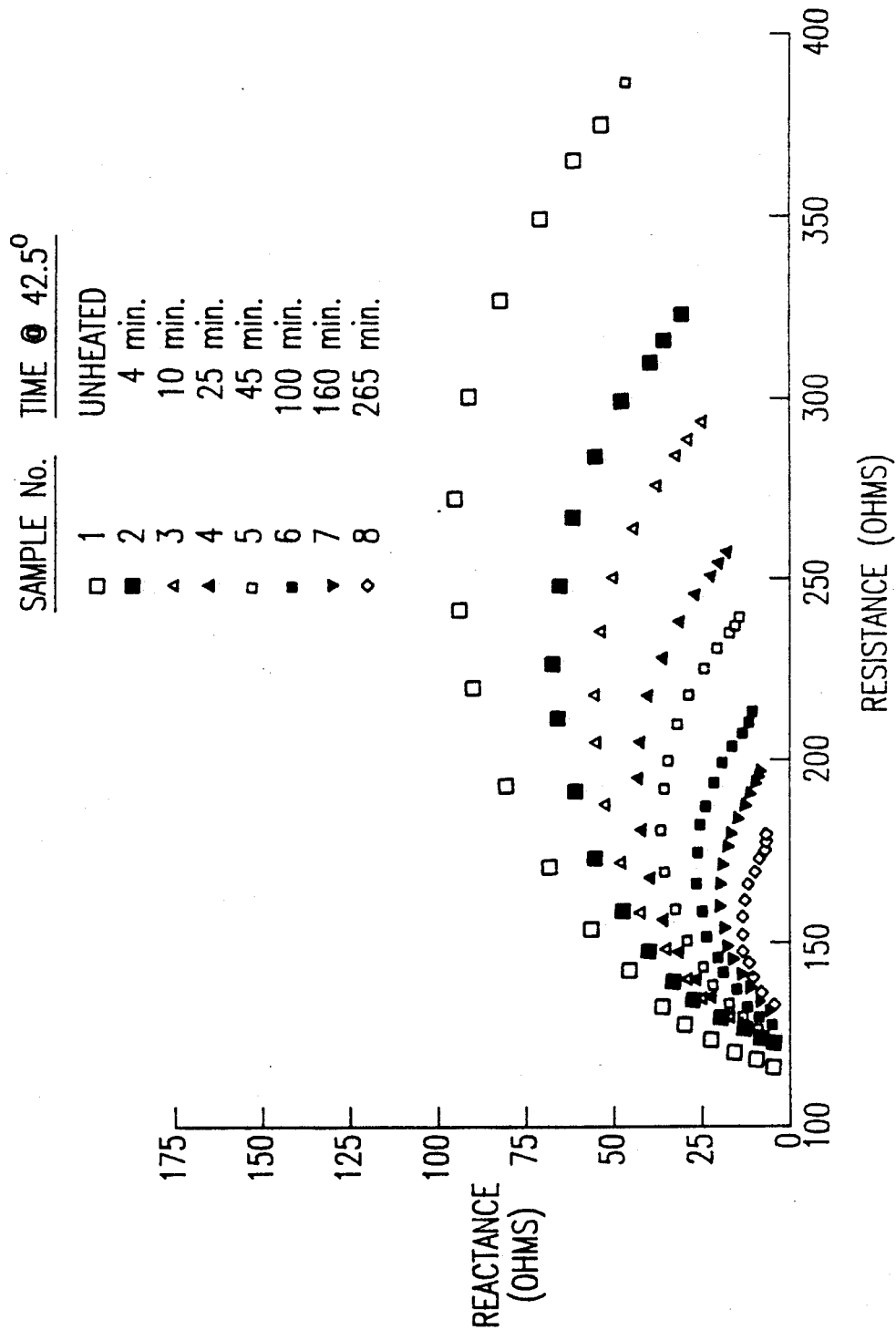
FIGS. 3 and 4 represent a set of plots of reactance versus resistance measured in vivo in the skeletal muscle of an anesthetized rat's hind leg.
Figure 4:
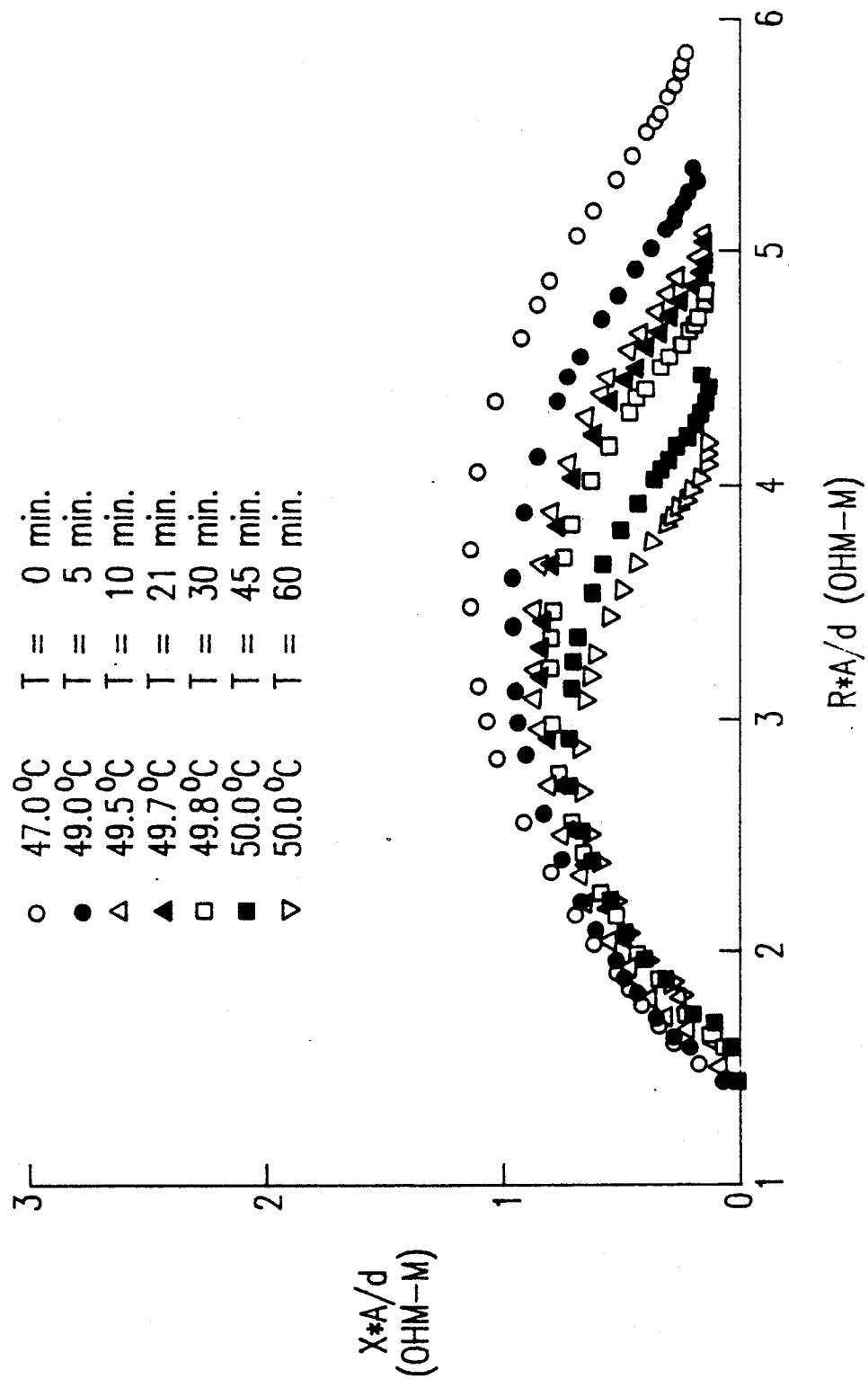

The following three FIGS. (2, 3, 4) are plotted in the resistance versus reactance (or resistivity versus reactivity) format for easy comparison with FIG. 1. It is seen that they resemble FIG. 1 in the decrease of the size of the semicircles towards the origin of the graph. The major differences to be noted in the following graphs are: 1) the time frame indicates changes occurring in minutes rather than days; and 2) the tissue shown is being exposed to therapeutic hyperthermia temperatures while being measured. It can be seen that the progress of tissue damage (or change), during the application of the therapeutic hyperthermia temperatures, is reflected in the changes in the electrically measured impedance of the tissues, both for excised tissue (FIG. 2), and in vivo (FIGS. 3 and 4). It can also be noted, if these plots are compared with FIG. 1, that the changes appear to be caused by the progressive breakdown of the cells or their membranes with increased time at hyperthermia temperature.

Figure 2:
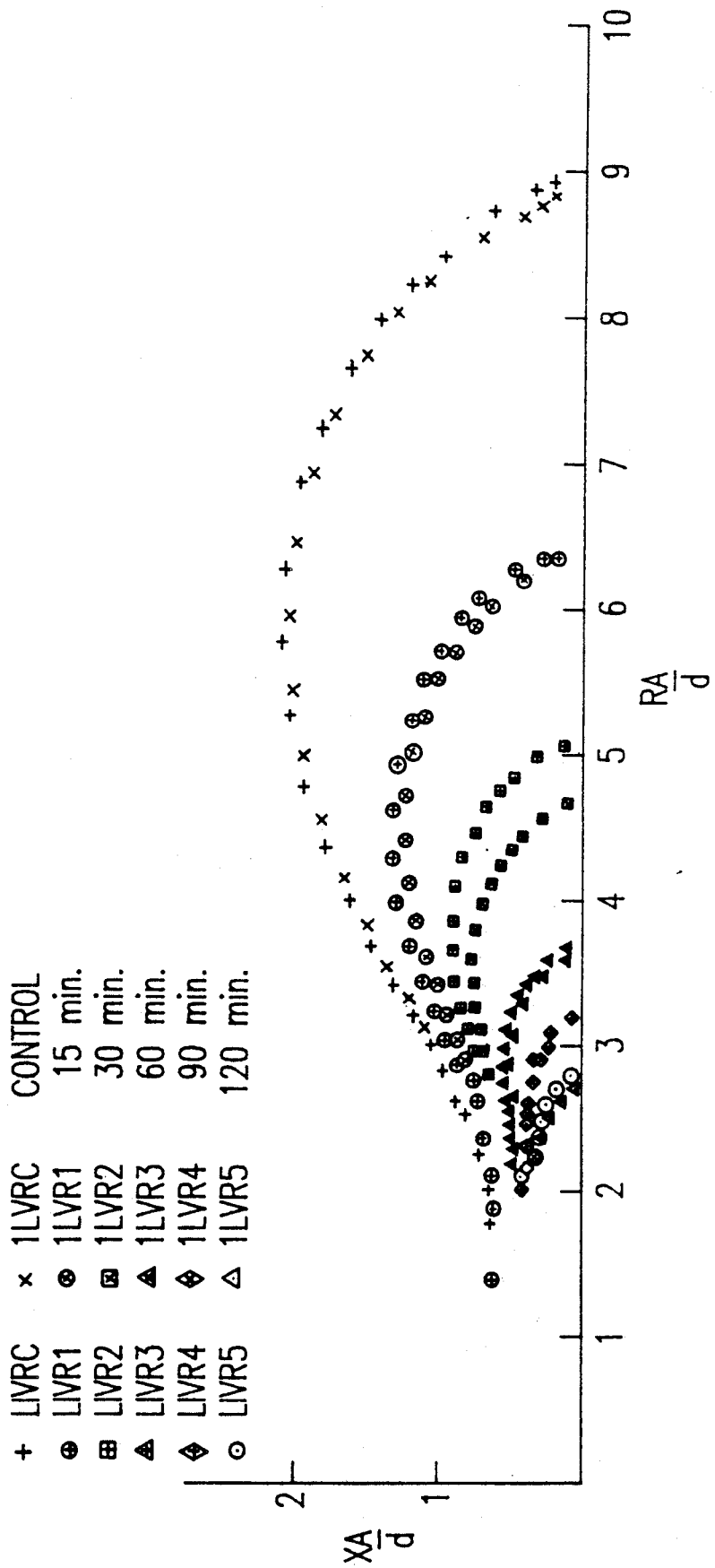
FIG. 2 represents a set of plots of the reactivity versus the resistivity of samples of fresh excised liver heated to 45° C. for varying lengths of time.

FIG. 2 is a set of plots of the reactivity (reactance multiplied by electrode area and divided by electrode separation, or XA/d) versus the resistivity (resistance*A/d or RA/a) of samples of fresh excised liver heated to 45° C. for varying lengths of time. This plot represents the $\beta$-dispersion of the liver tissue.

The plot shows data for twelve samples, two each for a control and for five different heating time at 45° C. The first (largest) curve represents unheated control samples. The following (shrinking) curves indicate the change in impedance after 15,30,60,90 and 120 minutes of heating at 45° C. It is seen that the $\beta$-dispersion has practically disappeared after 90 to 120 minutes.

FIG. 3 is a set of plots of reactance versus resistance measured in vivo in the skeletal muscle of an anesthetized rat's hind leg. The measurements were made with two platinum electrodes (1.25 mm diameter, 8 mm long, connected to insulated leads) implanted to the same depth at approximately midplane, parallel to each other, 10 mm apart. The muscle was heated using 1 MHz radio frequency power applied via implanted electrodes. The target temperature was measured halfway between the measurement electrodes at midplane depth. The large semi-circle "1" represents unheated tissue before the beginning of the hyperthermia. The following 7 decreasing semi-circles represent heating for progressively longer times of 4,10,25,45,100,160 and 265 minutes. It is seen that tissue changes resulting during hyperthermia administered in vivo are reflected in the measured electrical impedance of the tissue.

FIG. 4 is a set of plots of reactivity (XA/d) versus resistivity (RA/d) measured non-invasively in vivo in the skeletal muscle of an anesthetized rat's hind leg. The measurement electrodes were circular platinum of about 1 square centimeter area, placed parallel on the shaved, abraded and cleaned skin on opposite sides of the large skeletal muscle in the rat's hind leg. The tissue was heated using 1 MHz radio frequency power applied via implanted electrodes. The target temperature was measured approximately at midplane between the electrodes. The largest semi-circle represents unheated data taken before heating was begun. The next 6 decreasing semi-circles represent heating for progressively longer times (5,10,21,30,45 and 60 minutes). It is seen that tissue changes resulting from hyperthermia can be measured non-invasively, in vivo.

Figure 5:
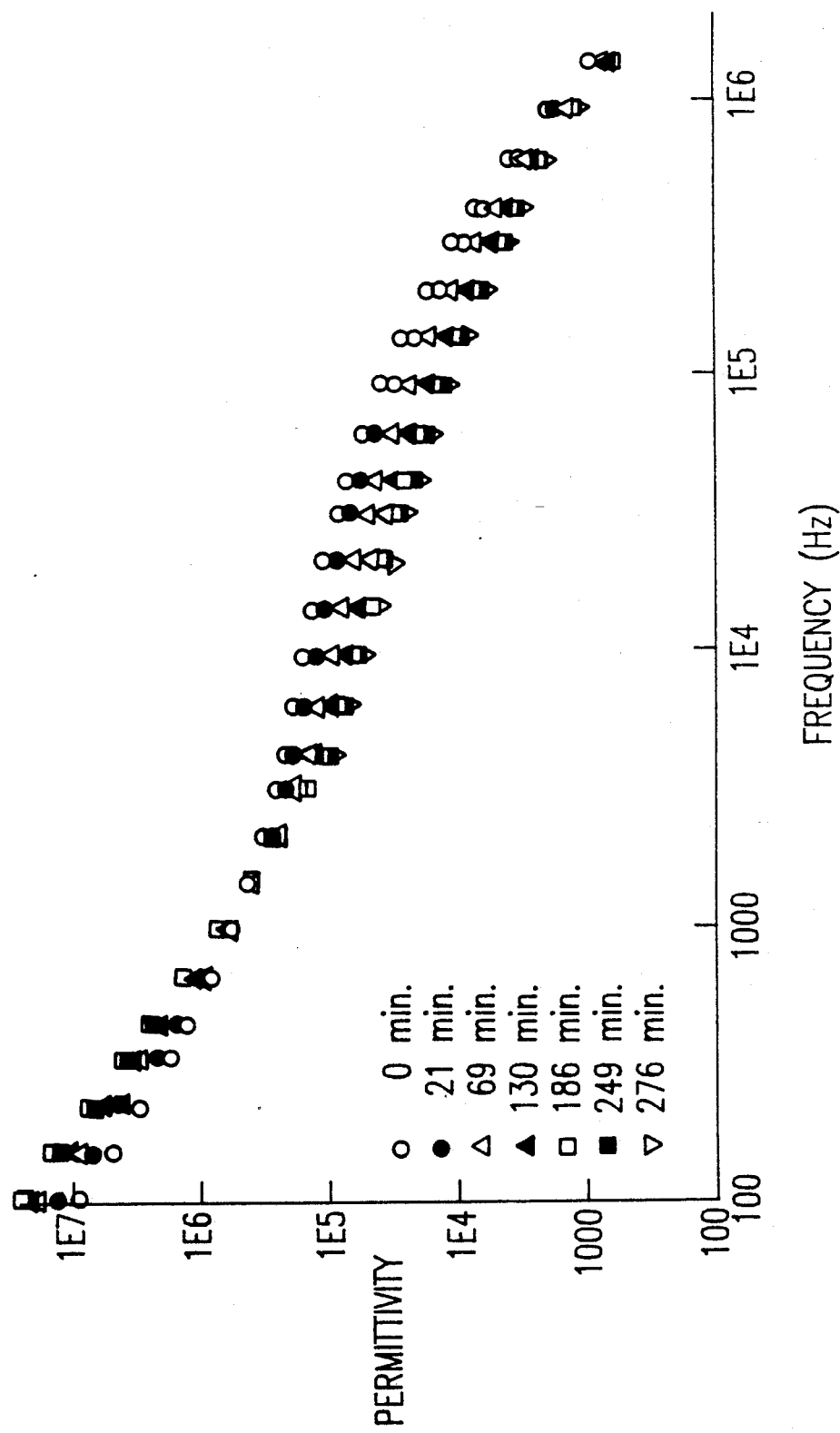
FIGS. 5 and 6 represent a plot of epsilon (permittivity or dielectric constant) versus frequency, and conductivity versus frequency, respectively.
Figure 6:
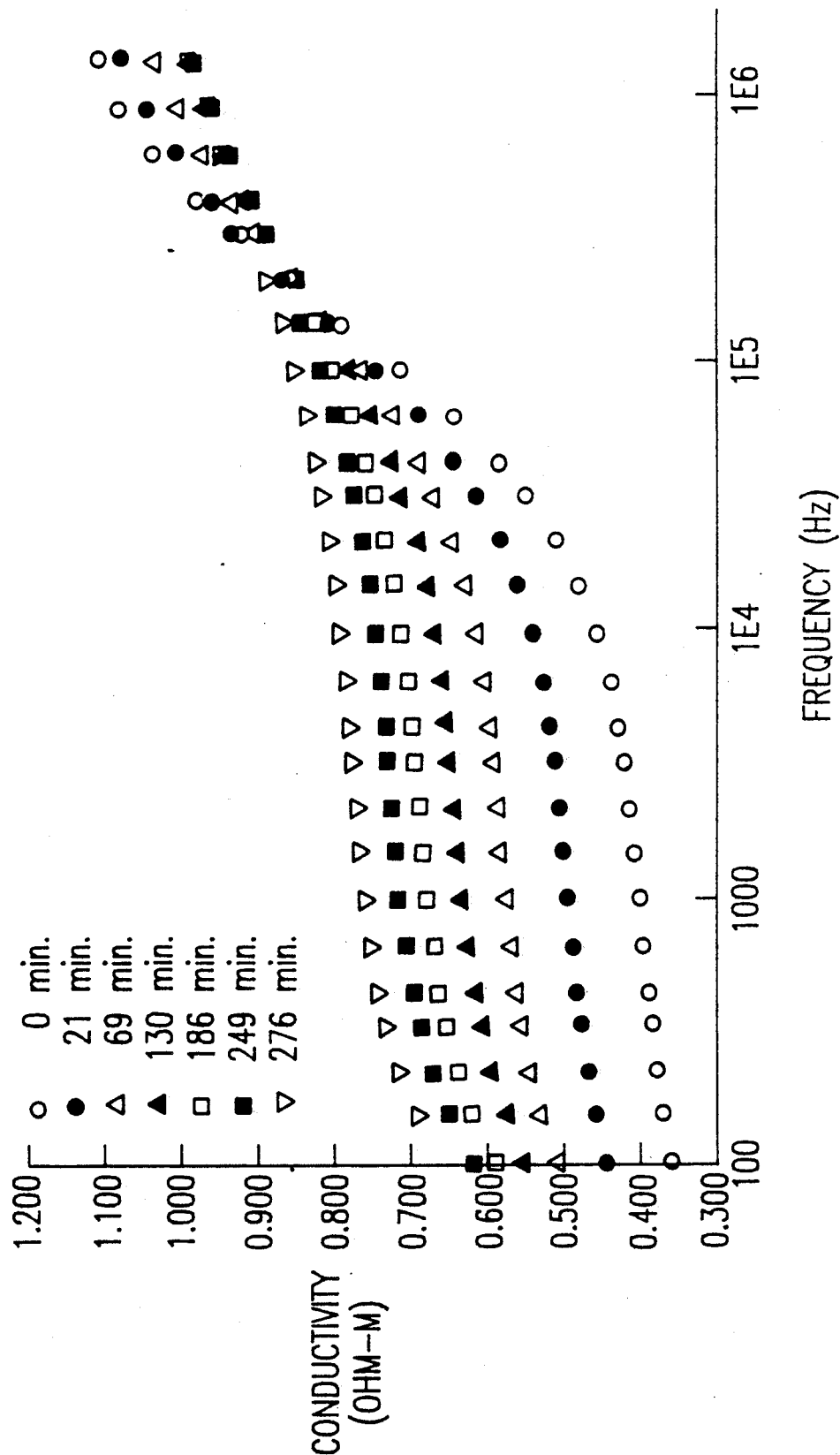

FIGS. 5 and 6 show epsilon (permittivity or dielectric constant) data versus frequency, and conductivity data versus frequency, respectively. These plots, for in vivo rat skeletal muscle show two more of the many methods of representing the measured electrical impedance data which can be used to show tissue change caused by hyperthermia. They show unheated data followed by heating data at 42.5° C. for various lengths of time, as indicated on the plots. Other plots may be shown of other representations, and some of these are be used below, for example.

Figure 7:
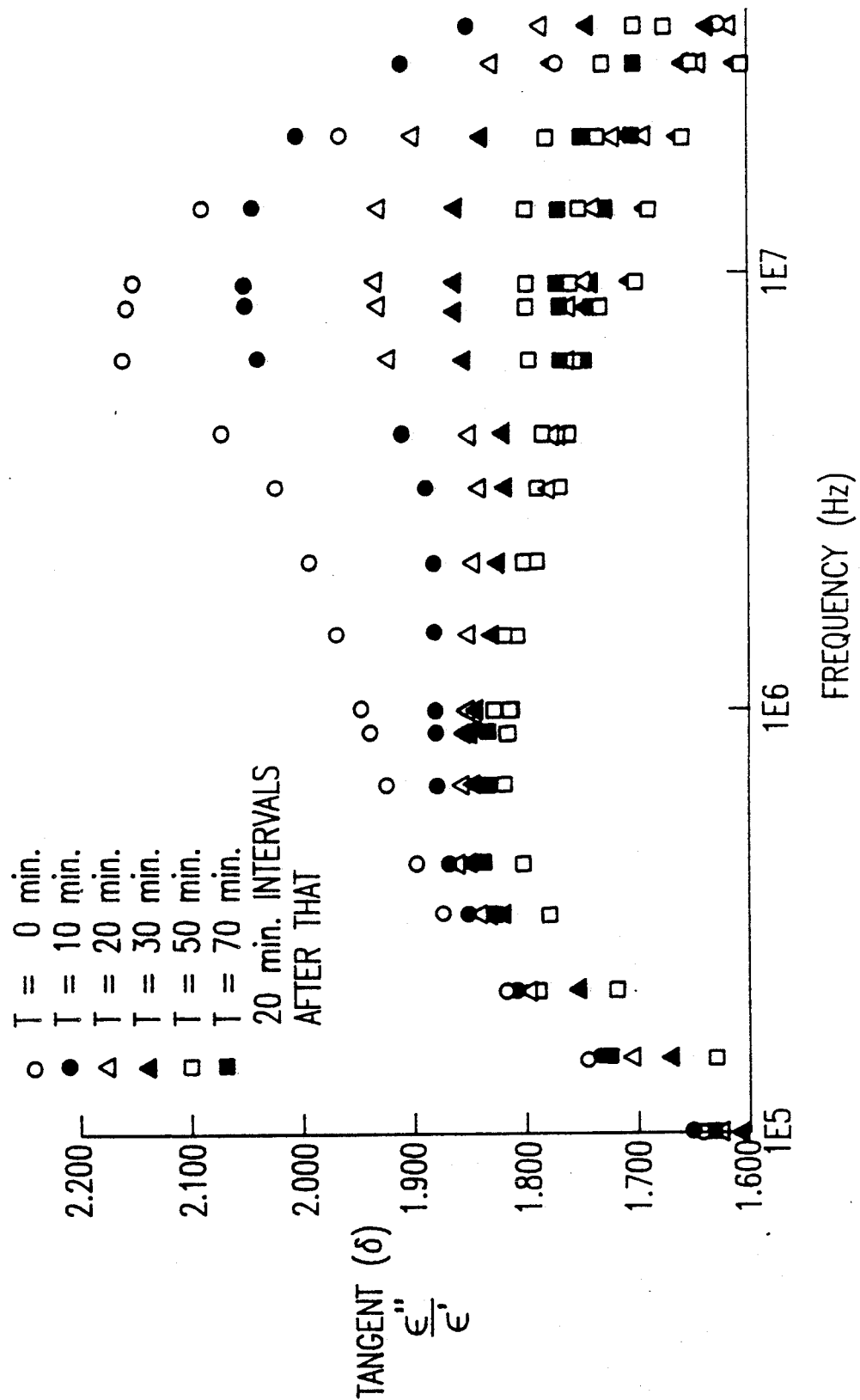
FIG. 7 illustrates a set of plots of tangent delta (epsilon double prime divided by epsilon prime) versus frequency for fresh excised rat kidney.

FIG. 7 is a set of plots of tangent $\delta$, ($\epsilon'$), versus frequency for fresh excised rat kidney. The tangent ($\delta$) representation shows another of the possible methods of resolving the tissue impedance data into yet another form. The tangent delta form is a manner of presenting the data assuming that it obeys theoretical tissue relaxation formulas such as those from Surowiec, A. and Stuchly, S. S. "Use of the Loss-Tangent Function in Dielectric Spectroscopy", *Bioelectromagnetics* p. 259-269, 1986 or 1987.

The largest plot is of fresh excised kidney as it has just reached 45° C. to begin a heating experiment. The following (increasingly smaller) plots indicate 10 minute intervals up to 30 minutes and then 20 minute intervals, thereafter. It can be seen that electrical impedance measurements can also show the changes occurring in kidney tissue during hyperthermia and that the tangent delta representation can be used to display these.

Figure 8:
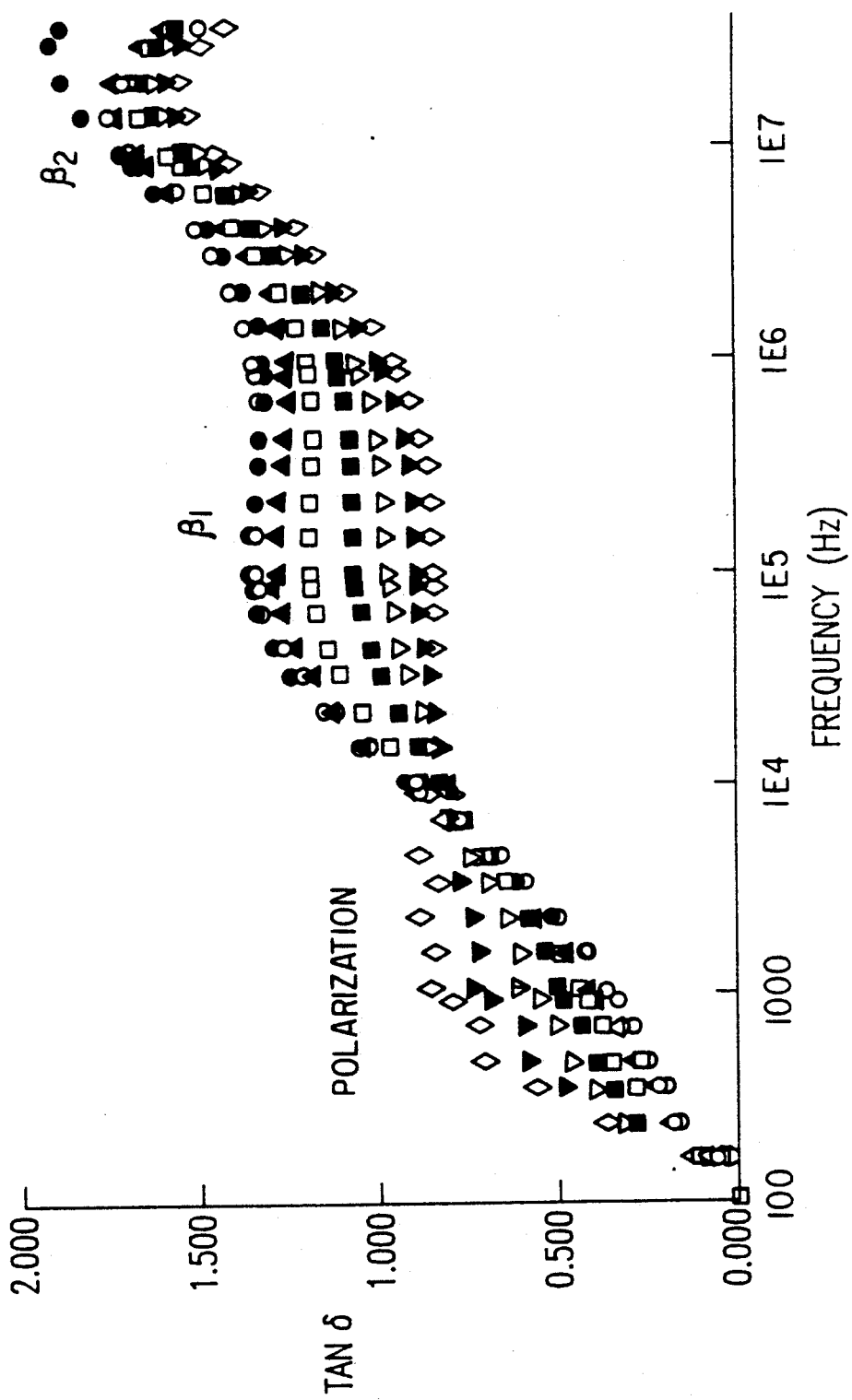
FIG. 8 represents a set of plots of tangent delta versus frequency for EMT-6 BALB/C mammary adenocarcinoma tumor grown subcutaneously in a BALB/C mouse.

FIG. 8 is a set of plots of tangent delta versus frequency for an EMT-6 BALB/c mammary adenocarcinoma tumor grown subcutaneously in a BALB/c mouse. These plots indicate three peaks. The first, at low frequency, labeled "polarization", increases with time and probably indicates the increase in actual and apparent electrode polarization as a result of the decreasing $\beta$-dispersion of the tissue and the increase of the number of ions in solution as a result of tissue damage. The next two decreasing peaks show changes resulting from applied hyperthermia to what may be two different cell-size populations within the tumor. The first curve, labeled "4" is measured as the tissue just reaches temperature at 45° C. The following curves are from data measured after 10,25,45,65,125,245 and 295 minutes of heating.

Figure 9:
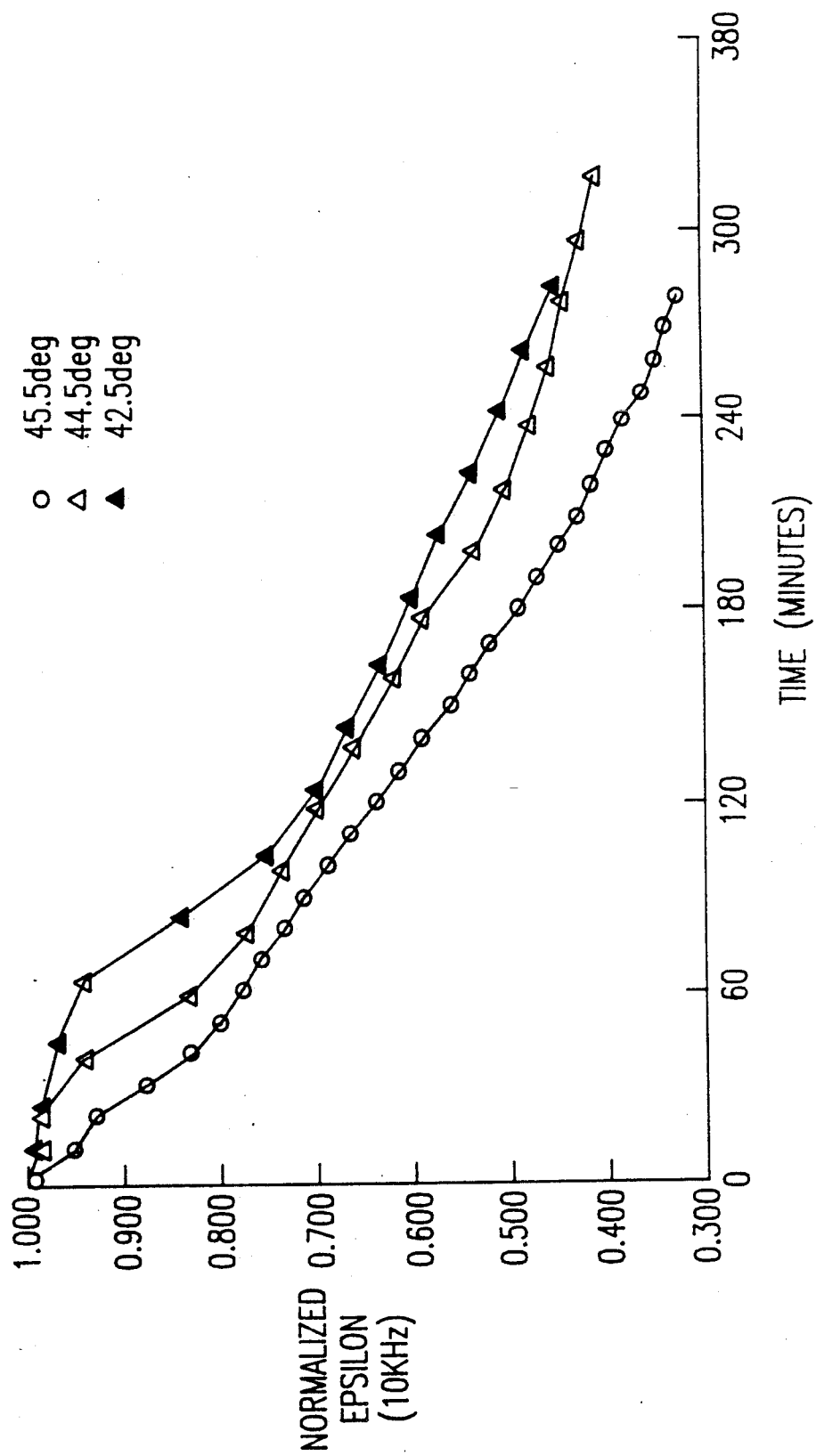
FIG. 9 illustrates three plots of epsilon (permittivity) versus heating time for three EMT-6 tumors heated at different temperatures.

FIG. 9 shows three plots of epsilon (permittivity) versus heating time for three EMT-6 tumors heated at different temperatures. This data has been normalized to the "zero time data" in order to show the relative changes in the different tumors. This data implies that increased heating temperatures accelerates the tissue changes caused by hyperthermia, even during the heating itself. Additional data for other tissues also tends to demonstrate this.

Information similar to this can be correlated with pathologically assessed tissue damage and clinical results, and used for future determination of the in vivo, real-time tissue effects occurring during and following hyperthermic treatment.

Presently, the hyperthermic treatment utilized with the present invention is effected at a temperature in the range of about 40° to 48° C., e.g., see *Biological, Physical and Clinical Aspects of Hyperthermia* (Med. Phys. Monograph No. 16 for the Amer. Assn. of Physicists in Medicine). However, temperatures may be used outside of this range. Further, the use of narrower temperature ranges within the above range is specifically contemplated. For example, temperature ranges of 40°-45° C., or 41°-44° C., or 42°-43° C. may be used as deemed appropriate.

Hereinbelow, an exemplary listing of equipment and apparati used in accordance with the present invention is provided. This listing is only provided for purposes of illustration and is not intended to be limitative.

EQUIPMENT IN GENERAL

General:
a collection of probes/sensors/electrodes;
materials and method for preparing electrodes; material or devices for placing the electrodes; connecting wires/conductors; electrical measurement apparatus; and hardware/software for analysis and display

SPECIFIC EQUIPMENT

Probes/electrodes/sensors are referred to as electrodes hereinbelow.

Electrodes may be of either platinum or platinum plated, silver/silver chloride, gold, stainless steel or other similar relatively non-reactive conducting materials, and may be of two general types: implantable/invasive or surface/non-invasive.

The implantable type is preferably in the form of small cylinders in the range of about 12-29 Gauge and having a length of about 1-20mm, or rectilinear devices of similar size. These have an electrical lead attached to them which is covered with an electrically insulating material extending up to where the connecting wires are attached from the measurement apparatus. These electrodes are manufactured in such a way as to have separate parts connected to different leads for providing different electrical signals to each part. These parts may be arranged in a paraxial, coaxial, or other manner and have separate leads connecting them to the measurement apparatus.

A few examples of possible types of invasive electrodes which may be used with this invention are described below.

An implantable probe of 1.75 inches long and 0.0957 inches (2.5 mm) diameter may be used containing two electrically separate platinum electrode portions, each 0.25 inches long and spaced 1.1 inches apart along the shaft. The tissue properties near the electrode are measured via electric fields created between the separate electrode portions. See, Schwan, H. P. and Kay, C. F. "Specific Resistance of Body Tissues", *Circulation Research* 4, p. 664-670, 1956.

Also, a 1.0 centimeter long probe may be used consisting of a 30-guage stainless steel inner shaft coated with epoxy and which is plated with a 15 micron layer of silver to form an outer coaxial electrode. The inner electrode is used for current injection and the outer for the voltage measurement. This electrode is moved through the tissue and the electrical impedance measured at various points in an attempt to establish the boundaries between different types of tissue. See, Organ, L. O. and Kwan, H. C. "Electrical Impedance Variation Along a Tract of Brain Tissue", *Ann. New York Acad. Sci.* 170, p.491-508, 1970.

Further, a number of coaxial-line sensors for in-vivo measurements may be used. For example, one consists of inner and outer coaxial conducting elements separated by teflon insulation. The end of the probe is placed on the tissue to be measured, either at the surface or within the tissue, and the measurement is via the electric fields generated at the end of the probe between the coaxial elements. See, Stuchly, M. A. and Stuchly, S. S. "Coaxial line reflection methods for measuring dielectric properties of biological substances at radio and microwave frequnces-a review", *IEEE Trans. Instru. Meas.* IM-29(3), p.176-183, 1980.

Moreover, a multisensor probe about 1 cm. long and 2 mm diameter containing four separate electrodes extending to different lengths at the end of the probe may be used. Measurements may be made between elements of a single probe or between different probes. See, Newbower, R. S. and Trautman, E. D. "Sensor for Catheter-Based Measurements of Electrical Conductivity", *IEEE Trans. Biomed. Eng.* Bme-33(2), p.182-188, 1986.

Other electrodes which may be used in the present invention are described in the section describing the drawings.

Many other possible electrode types, shapes and sizes may be used in accordance with the present invention and will be suggested to those skilled in the art in view of this disclosure.

Additionally, in accordance with the present invention, an invasive electrode may also be integrated with a number of other transducers on the same probes. For example, an electrode combined with temperature sensors may be used. Further, other probes, such as a pH probe, a blood flow sensor or an oxygen electrode, may be used in a multi-functional complex electrode.

The surface/noninvasive electrodes are preferably planar flat or curve-shaped conducting devices. In accordance with the present invention, a collection of these electrodes with various defined areas and shapes may be used which are made of similar materials as listed above. The electrodes have attached or attachable conducting leads which connect them to the electrical measuring device. These electrodes may be provided with "guard rings" or not as needed. These electrodes also may be arranged in the form of an array.

In accordance with the present invention, any type of surface electrode arrangement and placement is possible. For example, a flexible belt of insulating material with electrodes mounted on it may be placed on or wrapped around the body region of interest. Flexible or rigid linear arrays or separate electrodes may be used as well. A collection of some of the possible surface electrode types and arrangements which are well-known to those skilled in the art may be seen in the following publications:

*Electrical Impedance Tomography-Applied Potential Tomography*, in *Clinical Physics and Physiological Measurement, Special Issue*, Vol. 8, Suppl. A. 1987.

*INTRODUCTION TO BIOELECTRODES*, by Ferris, C. D., Plenum Press, New York, 1974.

Additionally, examples of electrodes which may be used in the present invention may be found in U.S. Pat, No. 4,291,708, and 4,458,694 which are incorporated herein in the entirety.

Commercial electrodes of various types usable in the present invention are available from Microelectrodes, Inc. Londonderry, N.H. 03053; and In vivo Metric, P.O. Box 249 Healdsburg, Calif. 95448; for example.

Material and methods for preparing electrodes

The electrodes may need to be prepared before use so as to limit the effects of electrode polarization. For example, platinization may be required, or some other form of preparation. If measurements are confined to 10kHz and above, polarization problems are usually negligible. Some well-known methods of platinization are described in the following publications:

*INTRODUCTION TO BIOELECTRODES*, by Ferris, C. D., Plenum Press, New York, 1974

Schwan, H. P., "Determination of Biological Impedances", *Phys. Tech. in Biol. Research.* 6, p.323–407, 1963.

It is also possible that sterile, minimally polarizable electrodes will be packaged and available commercially. If the electrodes are not sterile, then they may need to be sterilized in some manner.

Material or devices for placing the electrodes

The implantable electrodes may be placed using introductory needles. The electrodes will be placed within these needles, the needles inserted to the proper depth and position and then withdrawn while holding the electrode in place. These electrodes may also be made to be insertable without the aid of introductory needles. The surface electrodes may be placed directly on the surface of the patient. The area of placement may be prepared before-hand in a manner similar to that when placing EKG or other passive measuring electrodes and may or may not use conductive gels or other materials which aid in signal pickup. For example, surface electrodes may be arranged on a flexible or rigid device in the form or an array and placed on the surface of the patient in this form.

Connecting wires/conductors

Sets of wires, either plane, twisted pair, coaxially shielded or otherwise, may be used to connect the electrodes to the electrical measuring devices.

Electrical Measurement Apparatus

This apparatus will either be a means of applying an alternating current (AC) voltage to the electrode(s) and detecting the resulting AC current and/or its phase angle with respect to the applied voltage, or a means of applying an AC current to the electrodes and detecting the resulting AC voltage and/or its phase angle. Typical names for such devices are Impedance Analyzers, Network Analyzers, Electronic Bridges, Transformer Ratio-Arm Bridges, Phase Sensitive Detectors, Lock-in Amplifiers, Dielectric Spectrometers, etc.

EXAMPLE 1

As a non-limitative example of an impedance measurement device which may be used in accordance with the present invention, the following is noted. The specifications provided are for the Hewlett-Packard 4194A combined with the Hewlett-Packard 4194A/B. For more detailed specifications, reference may be made to the Hewlett-Packard 4194A data sheet.

Measurement Parameters:
$|Z|$, $|Y|$, $\Theta$, R, X, G, B, L, C, D and Q(1/D).
Twenty parameter combinations are available.

Frequency Range:
10 kHz–100 MHz, 1 mHz Resolution

Test Signal Level:
Opt. 350: 10 mV to 1.28 Vrms
Opt. 375: 10 mV to 1.54 Vrms

D.C. Bias:
Internal: ±40 V, ±20 mA
External: ±150 V, ±500 mA, max 25 W

Measurement Range:
10 m$\Omega$–1 M$\Omega$

Basic Measurement Accuracy
(at 25±5° C.)

$\geq$100 kHz: ±1.5% to 3%
$\leq$100 kHz: ±3% to 6%

Temperature Coefficient of Accuracy
$\leq$300 ppm/° C.

Level Monitor:
Opt. 350: 0 to 1.28 V, 0 to 52 mA
Opt. 375: 0 to 1.54 V, 0 to 42 mA Measurement Speed:
Typically 6 ms/point (at $\geq$30 kHz)

Cable Length:
41941A: 1.5 m
41941B: 3 m

Operating Temperature/Humidity
−20 to ±65° C.
Relative Humidity $\leq$95% at 40° C.

Storage Temperature
−40° C. to ±60° C.

Weight
41941A: Approx. 1.7 kg
41941B: Approx. 2.0 kg

Note: The HP 4194A must have Ver. 2.2 Software when using the HP 41941A/B.

An apparatus may be built having the capability of measuring at specifically selected frequencies in the range of 1 Hz to 100MHz. These frequencies are selected as providing the general dielectric or impedance information on the tissues being measured so as to be able to characterize the $\alpha$- or $\beta$-dispersion of the tissues and detect the changes in these dispersions which will best reflect the tissue damage and other changes occurring during hyperthermia. A greater number of frequencies may be used in order to more fully characterize the changes in the tissue(s) however any number of frequencies from 1 to about 20 may be used. Optimal frequencies for any given tissue are selected from the frequency ranges disclosed above. Some examples of electronic devices described above are described in the following sources, among others:

Technical literature on Impedance Analyzers from Hewlett Packard Inc.

Technical literature on Electrochemical Instruments and Lock-in Amplifiers from Princeton Applied Research, Inc., Princeton, N.J.

Stuchley, M. A. and Stuchly, S. S. "Coaxial Line Reflection Methods for Measuring Dielectric Properties of Biological Substances at Radio and Microwave Frequencies - A Review", *IEEE Reans. Instr. Meas.* IM29, (3), p.176–183, 1980.

Mopsik, F. I. "Precision Time-Domain Dielectric Spectrometer", *Rev. Sci. Instrum.* 55 (1), p.79–87, 1984.

Gregory, W. D. and Morelli, L. "Identification of materials using their complex dielectric response38", U.S. patent application Nos. 28452 and 847425, and U.S. Pat. No. 4,370,611, which patent is incorporated herein in the entirety.

Atlas, D. and Hasharon, H. "Electrical measuring system particularly useful for the non-invasive examination of biological tissue", U.S. Pat. No. 4,540,002, which patent is incorporated herein in the entirety.

Hardware/software for analysis and display

Analysis of the measurement data may take a broad range of forms. It may simply involve monitoring the change in one of the measured electrical components as a function of heating time. It may also involve the resolution of the measured data into one or more of the components of the complex impedance between electrodes. This resolution may involve the choice of a representative equivalent circuit for the situation. It may also involve knowledge of the geometric location and parameters of the electrodes and the further resolution of the impedance data into approximate tissue impedance information. Any of these may be performed at one or a number of frequencies. Ultimately, the resolved data will be analyzed either via an operator display or a preprogrammed set of instructions transforming this data into an operator display. The information of use may be the absolute magnitude or phase of a particular set of data, the relative magnitude or phase, or the rate of change of any of this data. Possible variables of use may be: measured current, measured voltage, measured phase angle; impedance or admittance; capacitance, conductance; approximate tissue parameters of permittivity, conductivity, or any of the other forms of the tissue complex admittance or impedance. Other possible variables may involve the fitting of the data to theoretical formula describing the behavior of tissue in an electric field or as a result of a particular equivalent circuit representation. Some of the variables extracted from this type of analysis are epsilon prime and double prime, sigma prime and double prime, tangent delta, sigma static, epsilon infinity, relaxation frequency, percentage cell concentration, for example.

While there seems to be a number of different ways of representing the data, these representations do not add any electrical information which is not already contained within the measured frequency dependent electrical currents, voltages and phase angles combined with a knowledge of the geometrical arrangement of the electrode(s), measured samples and surroundings; the available knowledge about the sample being measured and its surroundings; the knowledge of the shapes and properties of the electrodes themselves; and the knowledge of any stray or extraneous electrical signals, whether accidental or intended, which need to be taken into account.

Some of the variables discussed above are well-known and are described in the following publications:

Foster, K. R. and Schwan, H. P. "Dielectric properties of tissues", in *CRC Handbook of Biological Effects of Electromagnetic Fields*, CRC Press.

Hanai, T., Asami, K. and Koizumi, N. "Dielectric theory of concentrated suspensions of Shell-Spheres in Particular Reference to the Analysis of Biological Cell Suspensions". *Bull. Inst Chem. Res., Kyoto Univ.* 57, (4), 1979.

Surowiec, A. and Stuchly, S. S. "Use of the Loss-Tangent Function in Dielectric Spectroscopy", *Bioelectromag.* p. 259-269, 1986 or 1987.

Stoy, R. D., Foster, K. R., and Schwan, H. P. "Dielectric Properties of mammalian tissues from 0.1 to 100 MHz: a summary of recent data", *Phys. Med. Biol.* 27(4), p.501-513, 1982.

Having described the above, reference will now be made to another example which is provided solely for purposes of illustration and is not intended to be limitative.

EXAMPLE 2

A person with a cancerous lesion requires treatment which includes the use of hyperthermia.

During the treatment process, all parameters are recorded for use in later assessment of the treatment.

The location and extent of the lesion to be treated with hyperthermia, and the method of heating, desired temperature ranges and volumes to be heated are determined in accordance with known procedures. Adequate treatment planning is done, for example, using the actual measured patient parameters, either with computer or phantom simulation, and a plan and prescription for treatment devised. The means of electrical measurement of the tissue(s) is readied and included in the treatment planning process.

The patient is set up in the desired position and the heating applicator(s), additional bolus materials, surface cooling equipment, etc. are positioned for treatment. Either before, during or after (or continuously through all) the above equipment set-up, the electrical probes are implanted within and/or placed on or near the surface of the volume to be heated. The number and position of the probes are determined based on prior planning and clinical judgement at the time of placement. These probes are connected with a means for measuring the frequency-dependent electrical voltage and/or current and/or phase angle between them, as described previously. In addition, traditional temperature probes can be used.

Electrical measurements between probes or parts of probes are made as necesary, prior to beginning heating, during the heat-up phase, during the therapeutic heating phase, during the cooling-down phase, and after return to near normal body temperature. However, subsets of this information may also be used. Also during the electrical measurements the source of heating may be turned off momentarily, if necessary, to achieve the best accuracy.

The results of these electrical measurements are converted into absolute or relative information about the condition of the tissue(s). This may be done using a device which displays the desired electrical parameter(s), or their derivatives, on a plot versus time of heating.

The output of the abovementioned device may be used by the therapist or operator to observe the progression of tissue change occurring during the treatment. This will lead to possible changes in the applied heat in different regions during the treatment, determine the desired end-point of the heating, or aid in deciding other clinical parameters.

In addition, readouts may be obtained which display information about blood flow or volume changes as determined by frequency dependent analysis of the electrical data. Also, approximate temperatures may be determined from electrical property changes and displayed.

Also, the above data can be used to reconstruct an impedance image of desired parameters, (e.g., the change in a particular tissue electrical parameter such as resistivity which may give an image of the amount and extent of the tissue damage, blood volume changes, or temperatures). This image can be reconstructed as suggested by the known method of Applied Potential Tomography or by the process of William D. Gregory as discussed in U.S. patent application 147297, now issued as a U.S. Pat. No. and specifically incorporated herein in the entirety.

When the treatment, or desired measurement period, is completed, the electrical probes may be removed, or are allowed to remain in position for some time post-treatment for following further changes in the treated volume(s) of tissue. Alternatively, other probe arrangements may be used post-treatment for follow-up measurements.

After completion, the optimum electrical parameters are stored or recorded and are used as documentary evidence of the extent and amount of the treatment (e.g., as some indication of the 'thermal dose' delivered within certain volumes of tissue). This can be correlated with treatment outcome for use in future clinical application of the electrical measurement technique and determination of the parameters for better control of hyperthermia treatments and determination of treatment outcome.

Although the above-disclosed frequency ranges have been noted, any specific frequency or narrower frequency ranges within these ranges may be used. For example, a frequency of 100 Hz may be used, or a frequency range of 5 Hz to 1 KHz may be used.

Having provided the above description, it will be apparent to one of ordinary skill in the art that the above embodiments may be modified and changed while remaining within the spirit and scope of the present invention.

What is claimed as new and desired to be secured by Letters Patent of the United States is:

1. A method of evaluating tissue changes in a mammal occurring as a result of applying a therapeutic hyperthermia treatment to a volume of tissue of said mammal, comprising:
   a) placing electrodes on, near or into a volume of tissue to be monitored;
   b) applying therapeutic hyperthermia to the volume of tissue desired to be heated;
   c) measuring the electrical impedance of the volume of tissue to be monitored at least twice by means of the electrodes and by impedance measurement means in order to measure frequency dependent changes in the measured electrical impedance;
   d) employing the frequency dependent changes in the measured electrical impedance to evaluate physiological and histological changes in the tissue cells, thereby measuring the nature and extent of the tissue changes; and
   e) employing the measurements obtained from the tissue changes as a predictive assay of the progress of the hyperthermia treatment, thereby employing the same as an aid in adjusting the administration of the treatment, or determining a prognosis for each treatment, or ascertaining the desired stopping point for each treatment, or determining the need for further treatment or any combination of the above.

2. The method of claim 1, wherein said tissue is a soft tissue.

3. The method of claim 2, wherein said soft tissue is solid tumor tissue.

4. The method of claim 1, wherein said tissue electrical impedance is measured at one or more frequencies in the range of 1 Hz to 100 MHz.

5. The method of claim 4, wherein said tissue electrical impedance is measured at one or more frequencies in the range of 1 KHz to 100 MHz.

6. The method of claim 5, wherein said tissue electrical impedance is measured at one or more frequencies in the range of 10 KHz to 30 MHz.

7. The method of claim 1, wherein said mammal is a human.

8. The method of claim 1, wherein said therapeutic hyperthermia is applied to a human as a treatment for a solid tumor.

9. The method of claim 8, wherein said therapeutic hyperthermia is effected at a temperature of between about 40°–48° C.

10. The method of claim 1, wherein said changes in tissue electrical impedance are measured by non-invasive electrodes, invasive electrodes or a combination thereof.

* * * * *